(12) United States Patent
Bellwood et al.

(10) Patent No.: US 8,788,426 B2
(45) Date of Patent: Jul. 22, 2014

(54) HANDLING MEDICAL PRESCRIPTIONS IN A SECURE FASHION

(75) Inventors: Thomas A. Bellwood, Austin, TX (US); Anh Q. Lu, Austin, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/402,002

(22) Filed: Feb. 22, 2012

(65) Prior Publication Data
US 2012/0148049 A1 Jun. 14, 2012

Related U.S. Application Data

(62) Division of application No. 11/956,470, filed on Dec. 14, 2007.

(51) Int. Cl.
*G06Q 20/00* (2012.01)
*G06F 21/00* (2013.01)

(52) U.S. Cl.
USPC .......................................................... 705/64

(58) Field of Classification Search
USPC .............. 705/64, 16, 21, 59, 71; 380/44, 262, 380/278, 279
See application file for complete search history.

(56) References Cited

U.S. PATENT DOCUMENTS

| | | | | |
|---|---|---|---|---|
| 2001/0044886 | A1* | 11/2001 | Cassagnol et al. | 711/163 |
| 2006/0174110 | A1* | 8/2006 | Strom et al. | 713/165 |
| 2006/0265338 | A1* | 11/2006 | Rutkowski et al. | 705/71 |
| 2007/0083494 | A1* | 4/2007 | Carlson et al. | 707/3 |

OTHER PUBLICATIONS

Thomas A. Bellwood et al., U.S. Appl. No. 11/956,470, Office Action (Restriction) dated Apr. 16, 2010.
Thomas A. Bellwood et al., U.S. Appl. No. 11/956,470, Non-Final Office Action dated Jun. 24, 2010.
Thomas A. Bellwood et al., U.S. Appl. No. 11/956,470, Final Office Action dated Oct. 13, 2010.

* cited by examiner

*Primary Examiner* — Dante Ravetti
(74) *Attorney, Agent, or Firm* — Yudell Isidore Ng Russell PLLC

(57) ABSTRACT

Techniques for secure automated dispensing of prescription medications utilize broadcast encryption to encrypt a prescription for storage on a machine-readable medium that is pre-written with a key management block (KMB). The KMB encodes a session key needed to read from or write to the medium. Each prescription-writing device and medication dispensing device is assigned a unique set of device keys, which are used to recover the session key from the medium. Only authorized devices are able to recover the session key from a medium's KMB. Thus, only authorized devices may read or validly write prescriptions from/to the machine-readable medium. In this manner, only authorized providers can write fillable prescriptions and only authorized dispensers can dispense medications to fill those prescriptions.

15 Claims, 7 Drawing Sheets

| D(1,1) | D(2,1) | D(3,1) | D(4,1) |
|---|---|---|---|
| D(1,2) | D(2,2) | D(3,2) | D(4,2) |
| D(1,3) | D(2,3) | D(3,3) | D(4,3) |
| D(1,4) | D(2,4) | D(3,4) | D(4,4) |
| D(1,5) | D(2,5) | D(3,5) | D(4,5) |

| D(1,1) | D(2,1) | D(3,1) | D(4,1) |
|---|---|---|---|
| D(1,2) | D(2,2) | D(3,2) | D(4,2) |
| D(1,3) | D(2,3) | D(3,3) | D(4,3) |
| D(1,4) | D(2,4) | D(3,4) | D(4,4) |
| D(1,5) | D(2,5) | D(3,5) | D(4,5) |

Figure 1

| En[D(1,1),X(1)] | En[D(2,1),X(2)] | En[D(3,1),X(3)] | En[D(4,1),X(4)] |
|---|---|---|---|
| En[D(1,2),X(1)] | En[D(2,2),X(2)] | En[D(3,2),X(3)] | En[D(4,2),X(4)] |
| En[D(1,3),X(1)] | En[D(2,3),X(2)] | En[D(3,3),X(3)] | En[D(4,3),X(4)] |
| En[D(1,4),X(1)] | En[D(2,4),X(2)] | En[D(3,4),X(3)] | En[D(4,4),X(4)] |
| En[D(1,5),X(1)] | En[D(2,5),X(2)] | En[D(3,5),X(3)] | En[D(4,5),X(5)] |

$$X(1) \oplus X(2) \oplus X(3) \oplus X(4) = SK$$

Figure 2

HANDLING MEDICAL PRESCRIPTIONS IN A SECURE FASHION

This application is a divisional of U.S. patent application Ser. No. 11/956,470, entitled "CRYPTOGRAPHIC PRESCRIPTION SYSTEM," to Thomas A. Bellwood et al., filed Dec. 14, 2007, the disclosure of which is hereby incorporated herein by reference in its entirety for all purposes.

BACKGROUND

1. Field

The present invention relates generally to ensuring the privacy and authenticity of documents. In particular, the present invention is directed to preparing and reading medical prescriptions to/from electronic media in a secure fashion.

2. Related Art

As medical science as progressed, an ever larger number of conditions are either treated or prevented by prescription medications. Physicians prescribe and pharmacists fill more prescriptions for more different types of medications than ever before. This increase in the number and types of prescriptions being filled can easily result in a corresponding increase in the incidence of prescribing and dispensing errors, as well as an increase in undetected prescription forgeries and abuse.

Traditionally, prescriptions have been (and for the most part continue to be) handwritten and signed documents written on prescription pads pre-printed with the prescriber's name and contact information, much as a letterhead. This scheme, while long being a convenient system for prescribing physicians, suffers from a number of weaknesses that are troublesome or at best inconvenient for pharmacists, patients, and physicians.

While in the past, professional printing of prescription pads may have been largely sufficient to identify a prescription as coming from an official source, low-cost laser printing has made it possible for virtually anyone to produce professional-appearing stationery and convincing facsimiles of physicians' existing prescription pads with home-based equipment. To combat this potential for forgeries, particularly with respect to prescriptions for controlled substances, many professionally-printed prescription pads now employ such many of the same anti-forgery technologies used by financial institutions and reserve banks to prevent forgeries of negotiable instruments and currency, such as microprinting, thermally sensitive paper, non-photocopiable printing, and the like.

Another serious problem with handwritten prescriptions is legibility. Physicians, as a group, have long been notorious for writing illegible prescriptions. To address this problem, entire seminars devoted to handwriting improvement are held each year for members of the healthcare community. Another approach to this problem that is increasing in popularity, however, is to use computer software to not only print the prescriber's information (as with a pre-printed prescription pad), but also the actual medication and dosage being prescribed. An additional benefit of this approach is that the computer, with no additional effort on the part of the physician, can keep a record of all prescriptions written. Yet another benefit of using computers to print prescriptions is that computers can be programmed to store and utilize prescribing information about the medications being prescribed. Such information can be used to identify potential prescriber errors or other problems (such as improper dosages, potential adverse drug interactions or allergies) at the time the prescription is written, thus reducing the likelihood that a prescription error will go undetected.

A logical next step in the computerization of medical prescriptions is to automate not only the writing of prescriptions by doctors, but to automate the actual filling of the prescriptions. Test programs are underway by insurance companies to place medication dispensing machines into doctors' offices for use by physicians who wish to provide drug samples to patients. A further development would be to provide for automated dispensing of prescription medication sold in retail locations. One such dispensing device is described in U.S. Pat. No. 6,892,941 to Rosenblum, which relies on networked telecommunication between the doctor's office, an insurance company, and a retail pharmacy.

Current vending and e-commerce technology, however, fails to address many of the security and privacy concerns associated with automated medication dispensing, as well as some matters of practical convenience to the patient and to health care providers. In particular, an automated medication dispensing system should be capable of authenticating a prescription's validity, ensuring the security and privacy of prescription information, and insuring that prescription information has not been tampered with. It is also desirable that only licensed, authorized dispensing machines be allowed to dispense prescription medications. It is further desired that these goals be accomplished without the necessity of creating a centralized database of medical records, which is burdensome to provide as a practical matter and undesirable to the health care community because of privacy concerns What is needed, therefore, is a decentralized system for secure automated dispensing of prescription medications. The present invention provides a solution to this and other problems, and offers other advantages over previous solutions.

SUMMARY

Accordingly, the present invention provides a method, computer program product, and data processing system for secure automated dispensing of prescription medications without the necessity of maintaining a centralized database of medical information. A preferred embodiment of the present invention utilizes broadcast encryption to encrypt a prescription for storage on a machine-readable medium that is prewritten with a key management block (KMB). The KMB encodes a session key needed to read from or write to the medium. Each prescription-writing device and medication dispensing device is assigned a unique set of device keys, which are used to recover the session key from the medium. Only authorized devices are able to recover the session key from a medium's KMB. Thus, only authorized devices may read or validly write prescriptions from/to the machine-readable medium. Hence, only authorized providers can write fillable prescriptions and only authorized dispensers can dispense medications to fill those prescriptions.

The foregoing is a summary and thus contains, by necessity, simplifications, generalizations, and omissions of detail; consequently, those skilled in the art will appreciate that the summary is illustrative only and is not intended to be in any way limiting. Other aspects, inventive features, and advantages of the present invention, as defined solely by the claims, will become apparent in the non-limiting detailed description set forth below.

BRIEF DESCRIPTION OF THE DRAWINGS

The present invention may be better understood, and its numerous objects, features, and advantages made apparent to those skilled in the art by referencing the accompanying drawings, wherein:

FIG. 1 is an example diagram of a matrix of device keys used in a broadcast encryption scheme that may be employed in an embodiment of the present invention;

FIG. 2 is an example diagram of a key management block matrix used in a broadcast encryption scheme that may be employed in an embodiment of the present invention;

DETAILED DESCRIPTION

Figure 3:
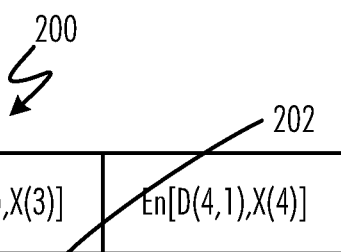
FIG. 3 is an example diagram of a key management block matrix containing a revocation used in a broadcast encryption scheme that may be employed in an embodiment of the present invention.

The following is intended to provide a detailed description of an example of the invention and should not be taken to be limiting of the invention itself. Rather, any number of variations may fall within the scope of the invention, which is defined in the claims following the description.

The present invention uses broadcast encryption to allow machine readable pharmaceutical prescriptions to be filled by authorized dispensing machines. Broadcast encryption is a form of cryptographic key establishment protocol that allows messages to be encrypted for reception by a dynamically defined set of authorized recipients where only one-way transmission is possible (such as in the case of a television broadcast, for example). In the case of the present invention, the authorized recipients are medicine-dispensing machines that have been authorized to fill medical prescriptions.

In a typical broadcast encryption scheme, a universe of random "device keys" is defined. Each potential recipient device is then assigned a subset of the full "device key" universe. No two devices are assigned the exact same subset of device keys, although the subsets are allowed to overlap so that any one particular key may be shared by a number of different devices.

Decrypting an actual message in a broadcast encryption scheme requires the recovery of a cryptographic key referred to herein as a "session key" from a "key management block" (abbreviated herein as "KMB"). In a basic sense, a KMB is a collection of multiple different encrypted versions of the session key, where the encrypted versions are encrypted using various device keys. An authorized device will be able to recover the session key by using one or more of its device keys to decrypt corresponding portion(s) of the KMB, thus obtaining the session key. Likewise, an unauthorized device will not be able to recover the session key from the KMB using the device keys it has been assigned. In this way, devices can be added or removed from the set of authorized recipient devices by creating a new KMB.

One particular broadcast encryption scheme is described in U.S. Pat. No. 7,039,803 to Lotspiech et al., which is assigned to the same assignee as the present application and also hereby incorporated by reference in its entirety. This '803 patent describes a broadcast encryption scheme in which the KMB contains copies of the session key encrypted with a carefully selected subset of the device key universe. Authorized devices need only possess one of the device keys used in compiling the KMB to recover the session key. This particular scheme is very useful for encrypting information intended for "stateless receivers," for which it cannot be assumed that the receiving device has received any previous transmissions.

Another broadcast encryption scheme is described in U.S. Pat. No. 6,118,873 to Lotspiech et al., which is assigned to the same assignee as the present application and also hereby incorporated by reference in its entirety. Unlike in the "'803 patent," the KMB employed in the "'873 patent" does not store encrypted copies of the actual session key. Instead, the universe of device keys is defined as a matrix, as in the example shown in FIG. 1. Each device is assigned a single key from each column in the matrix. For example, a device could be assigned the shaded keys from the matrix in FIG. 1, so that the device has a key from each column of the matrix.

The session key is derived by computing an exclusive-or (XOR) of a plurality of "session numbers," where the number of session numbers is the same as the number of columns in the device key matrix. Thus, for the example matrix in FIG. 1, which has four columns, the session key (SK) would be derived by "XOR-ing" four session numbers $X(1)$, $X(2)$, $X(3)$, and $X(4)$. The KMB, shown in FIG. 2, is then derived by encrypting the four session numbers with the device keys from the device key matrix. More specifically, the five device keys from each column are used to encrypt multiple copies of the session number associated with that column, thereby obtaining a KMB matrix having the same dimensions as the device key matrix.

An authorized device could therefore recover the session key by using each of its assigned device keys to recover the session number associated with each column in the KMB matrix and the XOR-ing the recovered session numbers together to obtain the session key. Devices' authorization is revoked by replacing session number information with dummy values in the KMB matrix. As shown in the example in FIG. 3, devices having been assigned device key $D(3,2)$ from the device matrix of FIG. 1 can have their authorization revoked by encrypting a dummy value in location 302 of KMB matrix 300 with device key $D(3,2)$ instead of $X(3)$, the third session number. When the unauthorized devices XOR the recovered "session numbers" together to obtain a session key, the value so obtained will be invalid, due to the inclusion of the dummy value instead of $X(3)$.

Either of these broadcast encryption schemes may be used in the context of the present invention. Additionally, other broadcast encryption schemes currently known in the art or that may be developed in the future may be used in place of the schemes described herein without departing from the scope or spirit of the present invention. Since the present invention is concerned with an application of broadcast encryption, rather than a means for providing broadcast encryption itself, the present invention need not be limited to the use of any particular broadcast encryption scheme.

Figure 4:
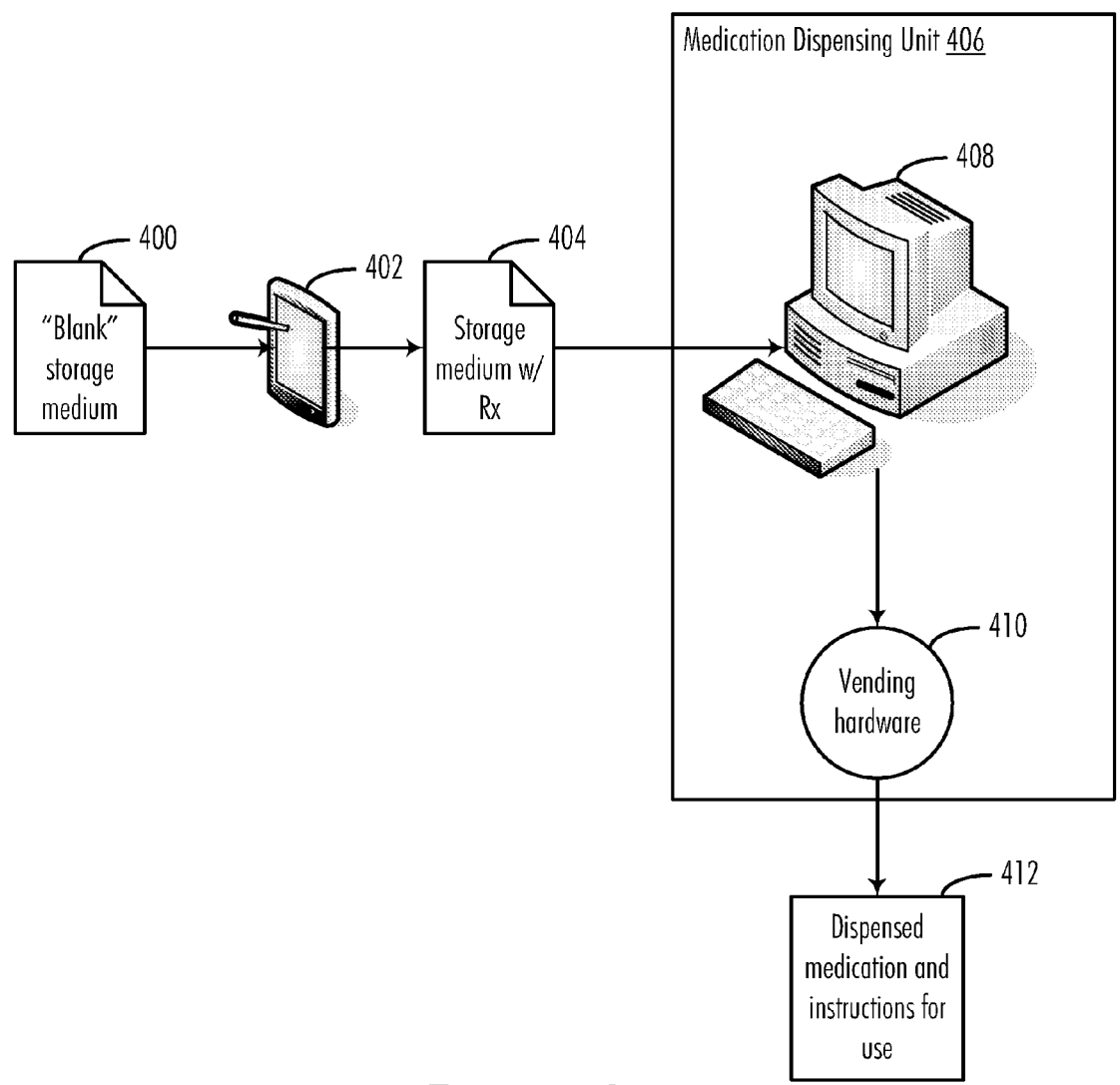
FIG. 4 is a diagram illustrating the overall operation of a preferred embodiment of the present invention.

Because it is desired that only legitimate vendors of pharmaceuticals be allowed to fill electronic prescriptions, the present invention uses broadcast encryption technology to ensure that only authorized dispensing devices (operated by legitimate retailers) be permitted to read patients' prescription information and fill prescriptions. A preferred embodiment of the present invention operates as shown in FIG. 4. The process begins with a "blank" storage medium 400. Medium 400 may be pre-written with a current KMB by the original source (e.g., manufacturer) of the medium or may be recorded with a current KMB by the prescriber. In a preferred embodiment medium 400 comprises a reusable electronic medium, such as a memory card or stick, although one skilled in the art will recognize that a multitude of different kinds of re-writeable and write-once computer readable media may be used without departing from the scope and spirit of the present invention. For example, one possible form of machine-readable medium that could be used in the context of the present invention would be a machine-readable pattern (such as a bar code) printed to ordinary paper. Yet another machine-readable medium would be a recordable optical or magnetic medium, such as an optical disc or magnetic card, the primary requirement being that the media have a tamper resistant means of unique identification which can be used to bind content recorded on it and thus prevent duplication.

A physician or other prescriber writes the prescription using a computing device such as handheld tablet computer 402. Tablet computer 402 uses its own set of device keys to obtain the session key for medium 400 from the KMB pre-written on medium 400 (or alternatively, from the latest KMB downloaded to tablet computer 402 from a central authority). Tablet computer 402 then uses the session key to write the prescription, in encrypted form, to medium 400 to obtain encrypted prescription 404, which is then presented to the patient.

The patient may then present the prescription to an automated medication dispensing unit 406 to have the prescription filled. Medication dispensing unit 406 comprises a computer system 408 to which is interfaced specialized vending hardware 410 for collecting payment and physically packaging and dispensing the medication. In response to receiving prescription 404, computer system 408 uses its own device keys to recover the session key, decrypts the encrypted prescription information using the session key, collects payment and/or insurance information from the patient/customer, and packages and dispenses the prescribed medication and any instructions for use to be included therewith 412.

If the prescription is refillable, encrypted prescription 404 (suitably modified to reflect the number of remaining refills) may be reissued to the patient for re-use. Alternatively, the patient's prescription information can be stored by computer system 408 to allow subsequent refills to be requested without encrypted prescription 404. In one possible embodiment of the invention, the automatic dispensing units are networked and/or communicate with a retailer's central data repository to allow the prescription to be refilled at multiple retailer locations. In any event, if encrypted prescription 404 is not returned to the patient for re-use, it should be collected by medication dispensing unit 406 for recycling or for possible re-programming with the latest KMB if the storage medium is to be re-used by another prescriber.

Figure 5:
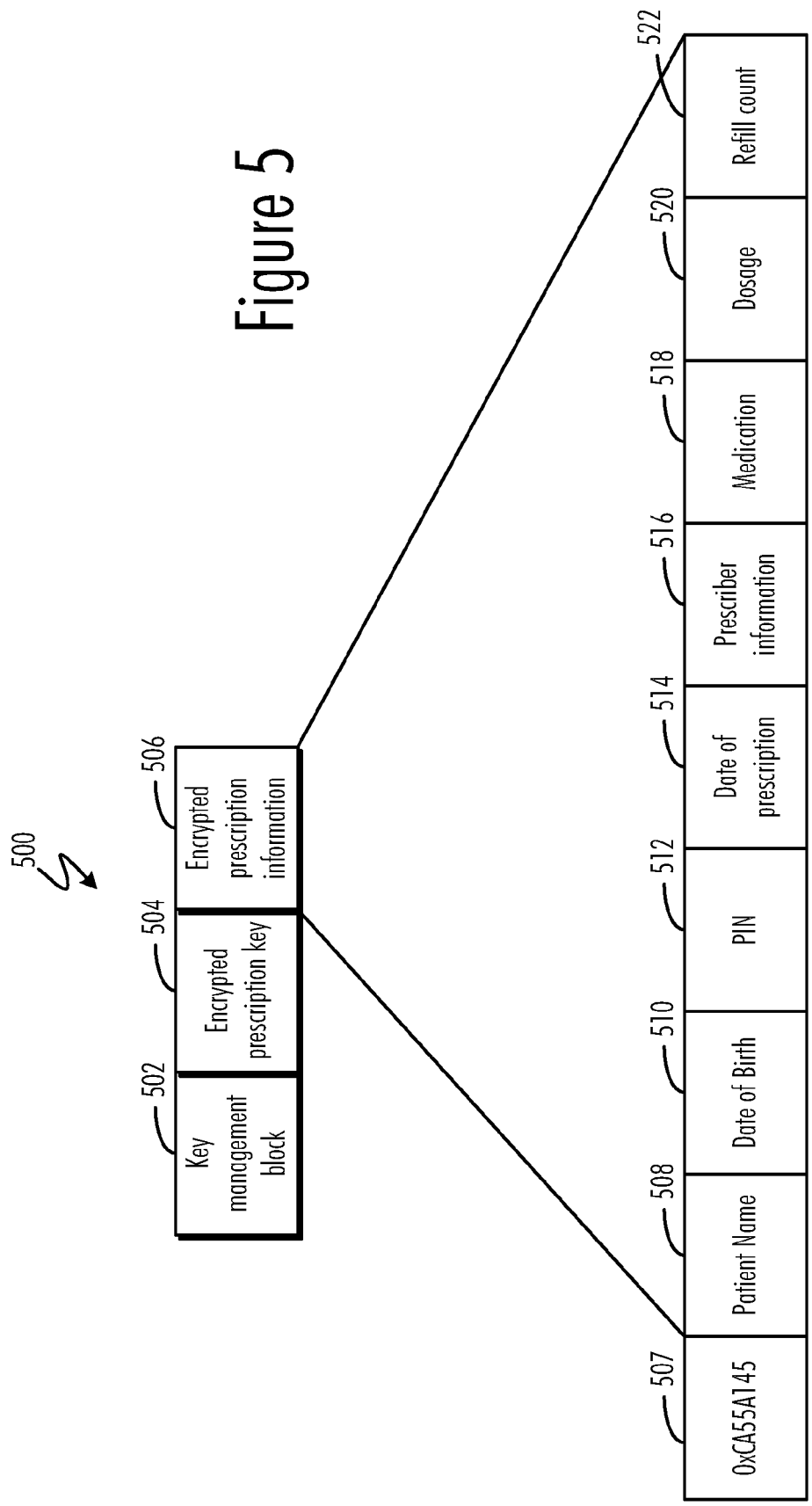
FIG. 5 is a diagram illustrating a format for encrypted prescriptions used in a preferred embodiment of the present invention.

The specific information 500 recorded on the prescription storage medium in a preferred embodiment of the present invention is described in FIG. 5. As stated previously, the key management block (KMB) 502 is pre-written to the storage medium by the manufacturer or other central authority. The prescription information itself 506 is stored in encrypted form such that it can only be decrypted using a "prescription key," which is itself stored in encrypted form (encrypted prescription key 504) on the storage medium. Prescription information 506 may be encrypted using any of a variety of different types of cryptosystems, including, but not limited to, conventional symmetric-key cryptosystems (such as the DES (Data Encryption Standard) cryptosystem described in U.S. Pat. No. 3,962,539 or the AES (Advanced Encryption System) cryptosystem described in Federal Information Processing Standard (FIPS) Publication 197 of Nov. 26, 2001).

Recovery of the prescription key from encrypted prescription key 504 is possible only by using the session key for the medium. The session key, of course, is obtained by using the decrypting (or, in the case of the prescriber's computer, encrypting) device's device keys to extract the session key from the pre-written KMB 502. The recovered session key can then be used as a decryption key to decrypt encrypted prescription key 504.

Alternatively, the session key and encrypted prescription key 504 could be combined in some other manner to obtain the actual prescription key. For example, the session key and encrypted prescription key 504 could represent two shares of the actual prescription key in a secret-sharing scheme, so that combining the two shares in the secret-sharing scheme yields the prescription key. Secret sharing is described generally in A. Shamir, "How to Share a Secret," Communications of the ACM, vol. 22, no. 11, pp. 612-613, November 1979.

The plaintext to encrypted prescription information 506 contains the actual prescription itself and is comprised of a number of data fields. The first of these is a pre-defined code number 507 that is used to verify that the decryption was successful. Other fields include the patient's name 508 and date of birth 510, the prescription date 514, the identity of the prescriber 516, the identity of the medication 518, dosage information 520, and a refill count 522 (indicating the number of refills available after the present prescription is filled. Additional authenticating information such as a personal identification number (PIN) 512 may also be included and required to be input at the time the prescription is filled to ensure that only the actual patient or the patient's agent may fill the prescription. Further, one skilled in the art will recognize that although information for only one medication is depicted in FIG. 5, information regarding multiple prescribed medications may be encoded on a single storage medium.

Figure 6:
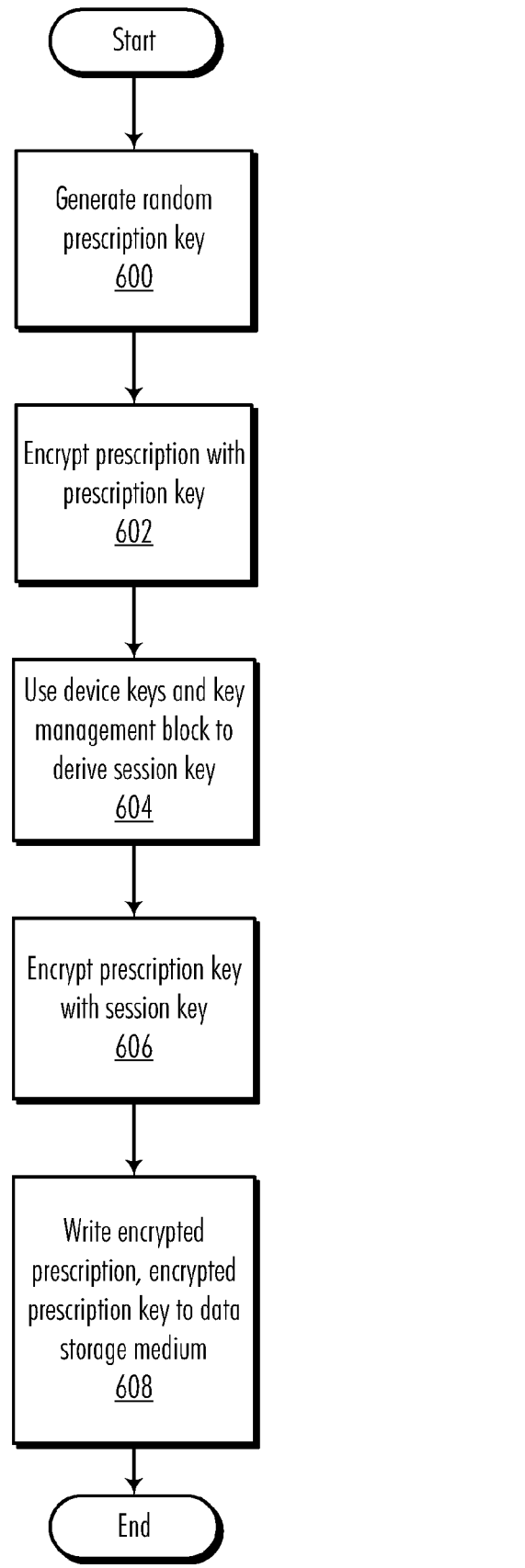
FIG. 6 is a flowchart representation of a process of encrypting a prescription using broadcast encryption in accordance with a preferred embodiment of the present invention.

A process of encrypting a prescription for writing to a storage medium by a prescriber device (device 402 in FIG. 4, for example) in the context of a preferred embodiment of the present invention is described more particularly in flowchart form in FIG. 6 as follows. This flowchart assumes that the actual prescription information has been entered by the prescriber into the prescriber device and needs only be encrypted and stored on the medium. First, a random prescription key is generated (block 600). The prescription is then encrypted using the generated prescription key and any suitable encryption algorithm (block 602). The prescriber device then uses its assigned device keys and the key management block (KMB) stored on the storage medium to recover the session key for the storage medium (block 604). The recovered session key is then used to encrypt the random prescription key generated previously (block 606). Finally, the encrypted prescription and the encrypted version of the prescription key used to encrypt the prescription are written to the storage medium for presentation to the patient (block 608).

Figure 7:
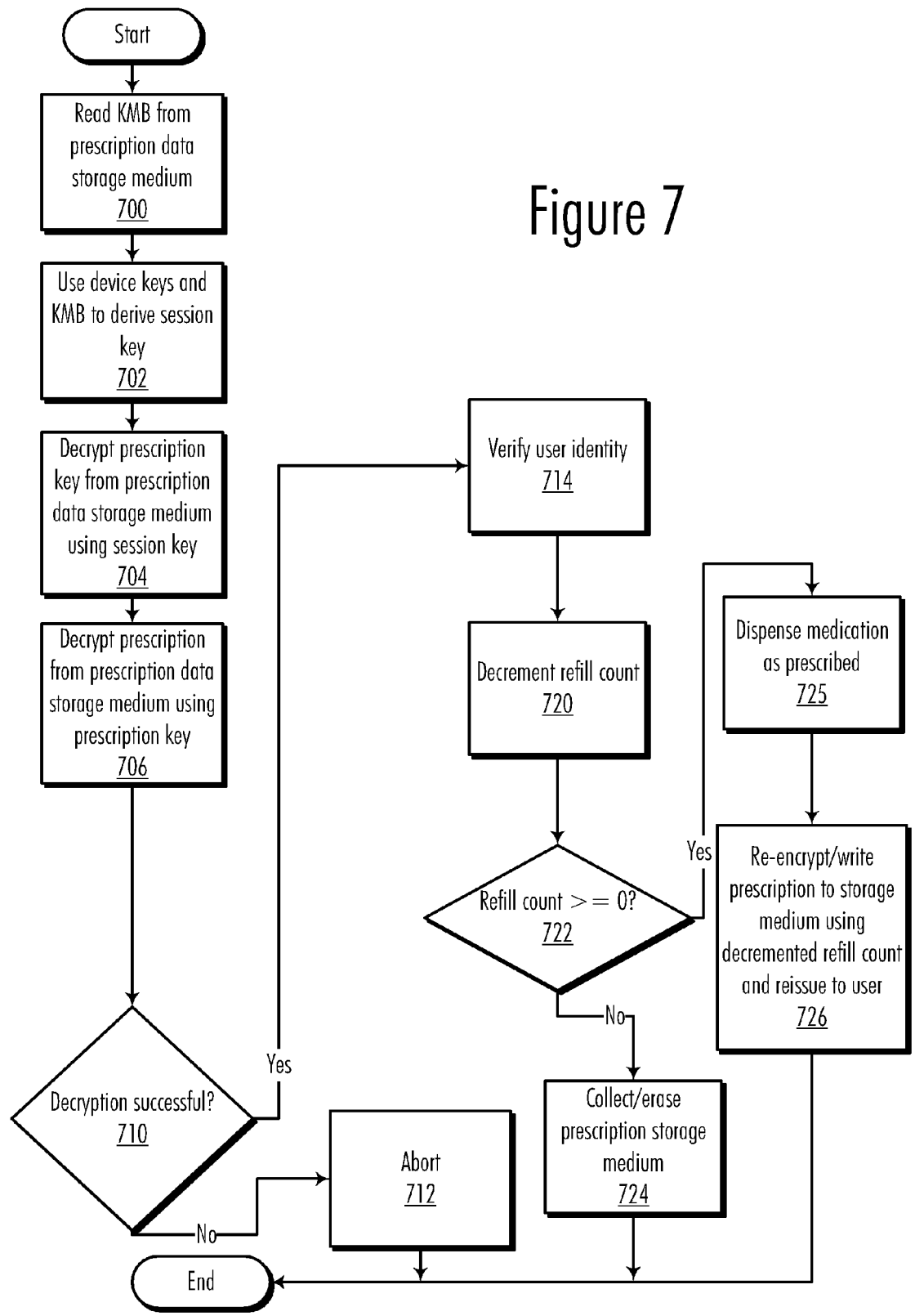
FIG. 7 is a flowchart representation of a process of decrypting and filling a prescription using broadcast encryption in accordance with a preferred embodiment of the present invention.

A process executable by an automated medication dispenser for decrypting and filling an encrypted prescription in a preferred embodiment of the present invention is described in flowchart form in FIG. 7. Upon receipt of the prescription storage medium, the dispenser reads the KMB from the medium (block 700). The dispenser then uses its set of device keys and the KMB to derive the session key for the medium (block 702). This session key is used to decrypt the prescription key from the medium (block 704). Next the actual prescription itself, including any authenticating information is decrypted from the storage medium using the prescription key (block 706). The results of the decryption are then verified to ensure that decryption was successful. If the decryption was not successful (block 710:No), the process aborts, as the dispenser is not an authorized medication dispenser.

If the decryption was successful (block 710:Yes), then the automated dispenser verifies the patient's identity (through name, date of birth, and/or PIN) (block 714). Next, the refill count from the prescription is decremented (block 720). If this decremented refill count is greater than or equal to zero (block 722:Yes), then the prescription is re-encrypted to the storage medium with the refill count adjusted to the new decremented value. The prescription is then filled as prescribed (block 725) and the storage medium is reissued to the user (block 726). Otherwise (block 722:No), the prescription storage medium is collected or confiscated by the prescription dispenser for subsequent erasure, reprogramming, or recycling (block 724). As noted previously, an alternative to this arrangement would be for the dispenser to always confiscate the storage medium and simply store the refill information in its own internal storage for use in preparing subsequent refills.

Figure 8:
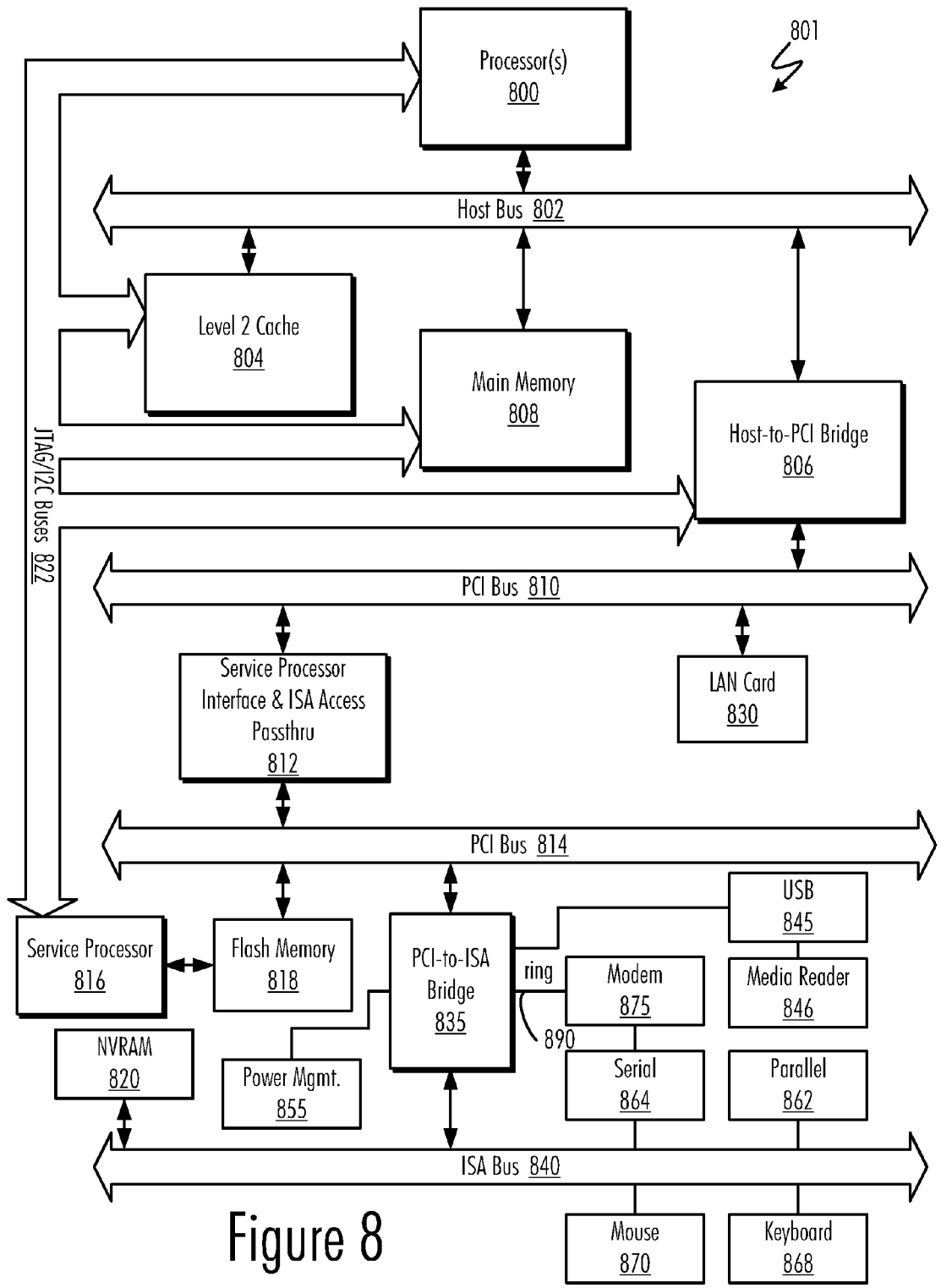
FIG. 8 is a diagram of a data processing system in which the processes of the present invention may be implemented.

FIG. 8 illustrates information handling system 801 which is a simplified example of a computer system/data processing system capable of performing the computing operations described herein with respect to a preferred embodiment of the present invention. Computer system 801 includes processor 800 which is coupled to host bus 802. A level two (L2) cache memory 804 is also coupled to host bus 802. Host-to-PCI bridge 806 is coupled to main memory 808, includes cache memory and main memory control functions, and provides bus control to handle transfers among PCI bus 810, processor 800, L2 cache 804, main memory 808, and host bus 802. Main memory 808 is coupled to Host-to-PCI bridge 806 as well as host bus 802. Devices used solely by host processor(s) 800, such as LAN card 830, are coupled to PCI bus 810. Service Processor Interface and ISA Access Pass-through 812 provides an interface between PCI bus 810 and PCI bus 814. In this manner, PCI bus 814 is insulated from PCI bus 810. Devices, such as flash memory 818, are coupled to PCI bus 814. In one implementation, flash memory 818 includes BIOS code that incorporates the necessary processor executable code for a variety of low-level system functions and system boot functions.

PCI bus 814 provides an interface for a variety of devices that are shared by host processor(s) 800 and Service Processor 816 including, for example, flash memory 818. PCI-to-ISA bridge 835 provides bus control to handle transfers between PCI bus 814 and ISA bus 840, universal serial bus (USB) functionality 845, power management functionality 855, and can include other functional elements not shown, such as a real-time clock (RTC), DMA control, interrupt support, and system management bus support. Nonvolatile RAM 820 is attached to ISA Bus 840. Service Processor 816 includes JTAG and I2C buses 822 for communication with processor(s) 800 during initialization steps. JTAG/I2C buses 822 are also coupled to L2 cache 804, Host-to-PCI bridge 806, and main memory 808 providing a communications path between the processor, the Service Processor, the L2 cache, the Host-to-PCI bridge, and the main memory. Service Processor 816 also has access to system power resources for powering down information handling device 801.

Peripheral devices and input/output (I/O) devices can be attached to various interfaces (e.g., parallel interface 862, serial interface 864, keyboard interface 868, and mouse interface 870 coupled to ISA bus 840. USB hub 845, for instance, is shown connected to a media reader 846 for the purpose of reading machine-readable tangible data storage media, such as memory cards, optical discs, and the like. Alternatively, many I/O devices can be accommodated by a super I/O controller (not shown) attached to ISA bus 840.

In order to attach computer system 801 to another computer system to copy files over a network, LAN card 830 is coupled to PCI bus 810. Similarly, to connect computer system 801 to an ISP to connect to the Internet using a telephone line connection, modem 875 is connected to serial port 864 and PCI-to-ISA Bridge 835.

While the computer system described in FIG. 8 is capable of executing the processes described herein, this computer system is simply one example of a computer system. Those skilled in the art will appreciate that many other computer system designs are capable of performing the processes described herein.

One of the preferred implementations of the invention is a computer program, namely, a set of instructions (program code) or other functional descriptive material in a code module that may, for example, be resident in the random access memory of the computer. Until required by the computer, the set of instructions may be stored in another computer memory, for example, in a hard disk drive, or in a removable memory such as an optical disk (for eventual use in a CD ROM) or floppy disk (for eventual use in a floppy disk drive), or downloaded via the Internet or other computer network. Thus, the present invention may be implemented as a computer program product for use in a computer. In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the required method steps. Functional descriptive material is information that imparts functionality to a machine. Functional descriptive material includes, but is not limited to, computer programs, instructions, rules, facts, definitions of computable functions, objects, and data structures.

While particular embodiments of the present invention have been shown and described, it will be obvious to those skilled in the art that, based upon the teachings herein, changes and modifications may be made without departing from this invention and its broader aspects. Therefore, the appended claims are to encompass within their scope all such changes and modifications as are within the true spirit and scope of this invention. Furthermore, it is to be understood that the invention is solely defined by the appended claims. It will be understood by those with skill in the art that if a specific number of an introduced claim element is intended, such intent will be explicitly recited in the claim, and in the absence of such recitation no such limitation is present. For non-limiting example, as an aid to understanding, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to inventions containing only one such element, even when the same claim includes the introductory phrases "one or more" or "at least one" and indefinite articles such as "a" or "an;" the same holds true for the use in the claims of definite articles. Where the word "or" is used in the claims, it is used in an inclusive sense (i.e., "A and/or B," as opposed to "either A or B").

What is claimed is:

1. A method of preparing computer-readable medical prescriptions, comprising:

encrypting, by one or more computers, a prescription for medication with a prescription key;

encrypting, by the computers, the prescription key;

creating, by the computers, an encrypted session key by encrypting session numbers of an unencrypted session key using device keys that are available at one or more authorized receiving devices, wherein the unencrypted session key is derived by logically combining the session numbers;

creating, by the computers, a key management block that includes the encrypted session key, wherein the encrypted session key is decrypted by the one or more authorized receiving devices in order to decrypt the encrypted prescription key;

writing, by the computers, the encrypted prescription key to a machine-readable medium;

writing, by the computers, the encrypted prescription to the machine-readable medium; and writing, by the computers, the key management block to the machine-readable medium.

2. The method of claim 1, further comprising:
encrypting, by the computers, the prescription key with the unencrypted session key.

3. The method of claim 1, further comprising:
identifying, by the computers, a plurality of devices to be cryptographically revoked that each include a subset of the device keys;
generating, by the computers, a new session key; and
encoding, by the computers, the new session key to form the key management block which cannot be decrypted using any of the subsets possessed by the identified devices.

4. The method of claim 3, wherein encrypting the prescription and encoding the new session key to form the key management block are performed by different ones of the computers.

5. A non-transitory computer-readable medium including stored instructions that, when executed by one or more computers, cause the computers to perform the method of:
encrypting a prescription for medication with a prescription key;
encrypting the prescription key;
creating an encrypted session key by encrypting session numbers of an unencrypted session key using device keys that are available at one or more authorized receiving devices, wherein the unencrypted session key is derived by logically combining the session numbers;
creating a key management block that includes the encrypted session key, wherein the encrypted session key is decrypted by the one or more authorized receiving devices in order to decrypt the encrypted prescription key;
writing the encrypted prescription key to a machine-readable device;
writing the encrypted prescription to the machine-readable device; and
writing the key management block to the machine-readable device.

6. The non-transitory computer-readable medium of claim 5, wherein the instructions, when executed by the computers, further cause the computers to perform the method of:
encrypting the prescription key with the unencrypted session key.

7. The non-transitory computer-readable medium of claim 5, wherein the instructions, when executed by the computers, further cause the computers to perform the method of:
identifying a plurality of devices to be cryptographically revoked that each include a subset of the device keys;
generating a new session key; and
encoding the session key to form the key management block which cannot be decrypted using any of the subsets possessed by the identified devices.

8. The non-transitory computer-readable medium of claim 7, wherein encrypting the prescription and encoding the new session key to form the key management block are performed by different ones of the computers.

9. A data processing system, comprising:
one or more computers; and
a computer-readable device including computer-readable instructions embodied on the computer-readable device, wherein the computer-readable instructions, when executed by the computers, cause the computers to perform the method of:
encrypting a prescription for medication with a prescription key;
encrypting the prescription key;
creating an encrypted session key by encrypting session numbers of an unencrypted session key using device keys that are available at one or more authorized receiving devices, wherein the unencrypted session key is derived by logically combining the session numbers;
creating a key management block that includes the encrypted session key, wherein the encrypted session key is decrypted by the one or more authorized receiving devices in order to decrypt the encrypted prescription key;
writing the encrypted prescription key to a machine-readable medium;
writing the encrypted prescription to the machine-readable medium; and
writing the key management block to the machine-readable medium.

10. The data processing system of claim 9, wherein the computer-readable instructions, when executed by the computers, further cause the computers to perform the method of:
encrypting the prescription key with the session key.

11. The data processing system of claim 9, wherein the computer-readable instructions, when executed by the computers, further cause the computers to perform the method of:
identifying a plurality of devices to be cryptographically revoked that each include a subset of the device keys;
generating a new session key; and
encoding the new session key to form the key management block which cannot be decrypted using any of the subsets possessed by the identified devices.

12. The data processing system of claim 11, wherein encrypting the prescription and encoding the new session key to form the key management block are performed by different ones of the computers.

13. The method of claim 1, wherein the logically combining includes exclusive ORing.

14. The computer-readable medium of claim 5, wherein the logically combining includes exclusive ORing.

15. The data processing system of claim 9, wherein the logically combining includes exclusive ORing.

* * * * *